United States Patent
Rajamäki

(10) Patent No.: US 8,118,796 B2
(45) Date of Patent: Feb. 21, 2012

(54) SUCTION BAG ARRANGEMENT

(75) Inventor: Veikko Rajamäki, Kauhajoki (FI)

(73) Assignee: Serres Oy (FI)

( * ) Notice: Subject to any disclaimer, the term of this patent is extended or adjusted under 35 U.S.C. 154(b) by 493 days.

(21) Appl. No.: 12/223,952

(22) PCT Filed: Feb. 9, 2007

(86) PCT No.: PCT/FI2007/050069
§ 371 (c)(1),
(2), (4) Date: Aug. 13, 2008

(87) PCT Pub. No.: WO2007/093670
PCT Pub. Date: Aug. 23, 2007

(65) Prior Publication Data
US 2009/0036847 A1    Feb. 5, 2009

(30) Foreign Application Priority Data
Feb. 13, 2006  (FI) ..................................... 20065107

(51) Int. Cl.
*A61M 1/00* (2006.01)
(52) U.S. Cl. ....................................... 604/319; 604/403
(58) Field of Classification Search .......... 604/317–320, 604/403, 408; 128/202.29, 205.15; 220/326; 137/205
See application file for complete search history.

(56) References Cited

U.S. PATENT DOCUMENTS

| | | | |
|---|---|---|---|
| 3,745,999 A | | 7/1973 | Deaton |
| 4,516,973 A | * | 5/1985 | Telang ........................... 604/319 |
| 5,671,861 A | * | 9/1997 | Hall et al. ................ 220/495.08 |

FOREIGN PATENT DOCUMENTS
EP    1642603    4/2006

OTHER PUBLICATIONS

Japanese Office Action dated Apr. 28, 2010 (with English translation, 3 pages).
Machine translation of JP -A-H09-056810.

* cited by examiner

*Primary Examiner* — Tatyana Zalukaeva
*Assistant Examiner* — Benedict L Hanrahan
(74) *Attorney, Agent, or Firm* — Seyfarth Shaw LLP

(57) ABSTRACT

An arrangement in connection with the handling of patient fluids, comprising a suction canister open at one end, a cover for closing the suction canister, a suction bag fastened to the cover, and an underpressure apparatus for applying underpressure to a space between the suction canister and the suction bag. The arrangement further comprises fastening means for keeping the suction bag narrowed in such a manner that the width and length of the suction bag are at least along part of the suction bag smaller than when the suction bag is opened, and the fastening means are arranged to release the suction bag to be opened into the suction canister under the action of the underpressure when the cover is closed.

7 Claims, 3 Drawing Sheets

SUCTION BAG ARRANGEMENT

This application is a U.S. National Phase of International Patent Application Serial No. PCT/FI2007/050069, filed Feb. 9, 2007 which claims priority to Finnish Patent Application No. 20065107 filed Feb. 13, 2006.

FIELD

The invention relates to an arrangement and a method for collecting material, such as patient fluids, to be handled in connection with a patient operation. The invention particularly relates to a suction bag arrangement to be used in collecting material, the suction bag comprised thereby being manufactured from flexible plastic.

BACKGROUND

Patient fluids, such as blood or interstitial fluid, created in connection with surgery at hospitals, or irrigation liquid used in irrigating a patient, may be collected into disposable plastic bags, so-called suction bags, for example. Suction bags may be placed in disposable suction canisters that are open at one end. The suction canister is closed with a cover to which the suction bag is fastened.

Underpressure applied to the inside of the suction bags makes the patient fluids transfer into the suction bags through a patient tube. Underpressure is typically also generated in a space between the suction canister and the suction bag in order for the suction bag to be spread evenly in the suction canister and in order to prevent it from collapsing under the action of the underpressure inside the suction bag.

The underpressure may be generated in the suction canister either from a separate device or from an underpressure network in such a manner that the underpressure source is connected through an underpressure tube to the cover of the suction canister or to the suction canister. The patient tube at the patient end, in turn, comprises a catheter for suctioning the fluids from the patient.

As regards manufacturing material, suction bags may be coarsely divided into two types, rigid and flexible. The problem in rigid bags is the large packaging size, which causes problems for logistics and storage. In use, when the suction bag is placed into the suction canister, a rigid bag structure may be difficult to fit into the suction canister.

The advantage of flexible, collapsible suction bags is a small packaging size, which provides significant advantages for logistics and storage. In accordance with the prior art, a suction bag fastened to the cover in connection with the placement of flexible suction bags is straightened before the suction canister is closed with the cover. Once the suction bag is straightened, the cover is fitted onto the suction canister. The width of a suction bag is known to be substantially in the order of the diameter of the suction canister, whereby the risk exists that part of the bag remains between the cover and the upper edge of the suction canister. Thus, the suction bag is not able to straighten properly in the suction canister, which could lead to the cover not being tightly arranged in place.

The straightening of the suction bag constitutes an extra step in the introduction of a suction arrangement. Insufficient training or a human error may cause the above-described type of error situation in connection with the placement of the suction bag. The likelihood of error situations is particularly high in emergencies, when it is important to place the suction bag rapidly in position.

BRIEF DESCRIPTION OF THE INVENTION

The object of the invention is thus to provide an improved method and an apparatus for implementing the method for collecting material, such as patient fluids, to be handled in connection with a patient operation.

The invention thus relates to an arrangement in connection with a patient operation, comprising a suction canister open at one end, a cover for closing the open end of the suction canister, and a suction bag fastened to the cover and placeable in the suction canister for collecting material to be handled in connection with a patient operation. The arrangement comprises one or more fastening means for keeping the suction bag narrowed in connection with being adapted to the suction canister in such a manner that the width and length of the suction bag, when it is narrowed, are at least along part of the suction bag smaller than when the suction bag is opened.

The invention also relates to a suction bag to be adapted to a suction canister for collecting material to be handled in connection with a patient operation, the suction bag being fastened to a cover intended for closing the suction canister. The suction bag comprises one or more fastening means for keeping the suction bag at least partly narrowed in the lateral and longitudinal directions in connection with being adapted to the suction canister.

The invention also relates to a method in connection with a patient operation, in which method material to be handled in connection with the patient operation is suctioned with a suction arrangement comprising a suction canister open at one and, a cover for closing the suction canister and a suction bag fastened to the cover and placeable in the suction canister for collecting the material. The method comprises placing the suction bag into the suction canister, the suction bag being fastened with one or more fastening means in a narrowed position in such a manner that at least part of the suction bag remains narrowed in the lateral and longitudinal directions in connection with the fitting in place of the cover.

An advantage of the invention is that when the suction bag is taken into use, it settles and straightens reliably in the suction canister. The placement into the suction canister does not require any specific actions, such as straightening the bag or guiding it into the suction canister manually. This crucially reduces placement errors and any problem situations they may cause.

BRIEF DESCRIPTION OF THE FIGURES

In the following, the invention will be described in more detail in connection with preferred embodiments with reference to the accompanying drawings, in which.

DETAILED DESCRIPTION OF THE INVENTION

Figure 1:
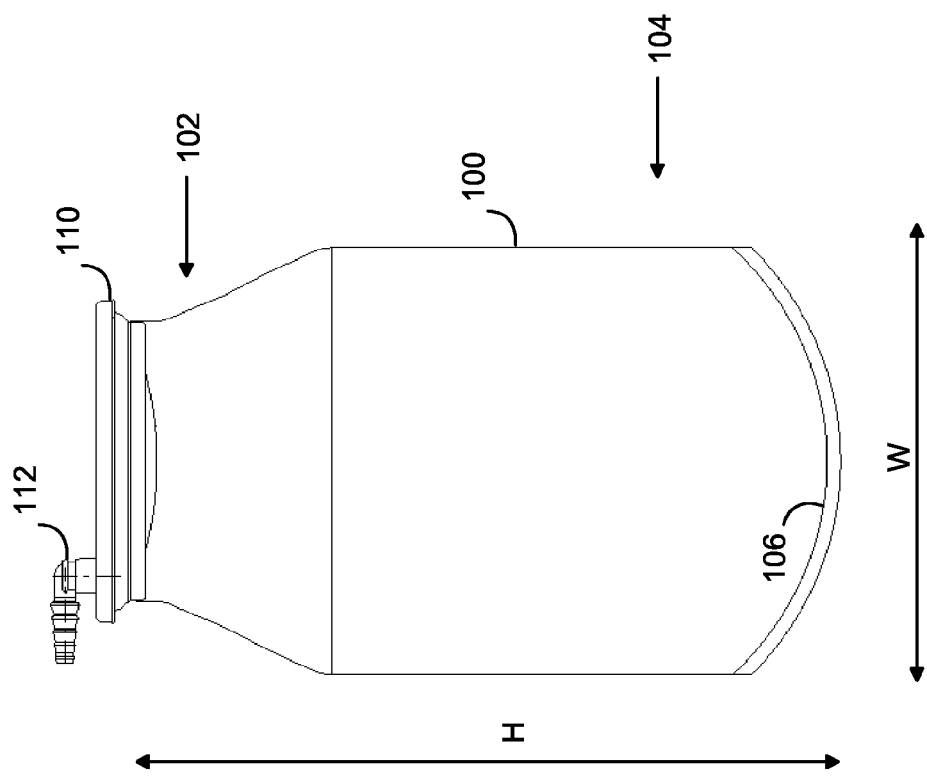
FIG. 1 illustrates a first embodiment of a suction bag arrangement.

FIG. 1 shows an embodiment of a suction bag arrangement. The arrangement comprises a suction bag 100 fastened to a cover 110 intended for closing a suction canister. Material, such as patient or irrigation fluids, to be handled in connection with a patient operation may be collected/suctioned into the suction bag. In addition to or instead of fluids, solid particles, such as bone fragments or gaseous materials, such as smoke, formed in connection with the patient operation may also be collected into the suction bag. In connection with the description, a material to be handled in connection with a patient operation thus refers to patient fluids, irrigation fluids, patient-originating solid materials or gaseous materials generated in connection with the operation, for example.

A top portion 102 of the suction bag represents the part of the suction bag adjacent to the cover, and a lower portion 104 is the most distant part of the suction bag with respect to the cover 110. FIG. 1 shows the suction bag 100 in an open position, wherein the maximum width of the suction bag in the lateral direction may be W and the maximum length in the longitudinal direction may be H. The figure shows that the width in the longitudinal direction is not necessarily constant, but the top of the suction bag may narrow towards the cover 110. FIG. 1 also shows a sealed bottom 106 of the suction bag. The cover may include a connector 112 for connecting a patient tube.

Figure 2:
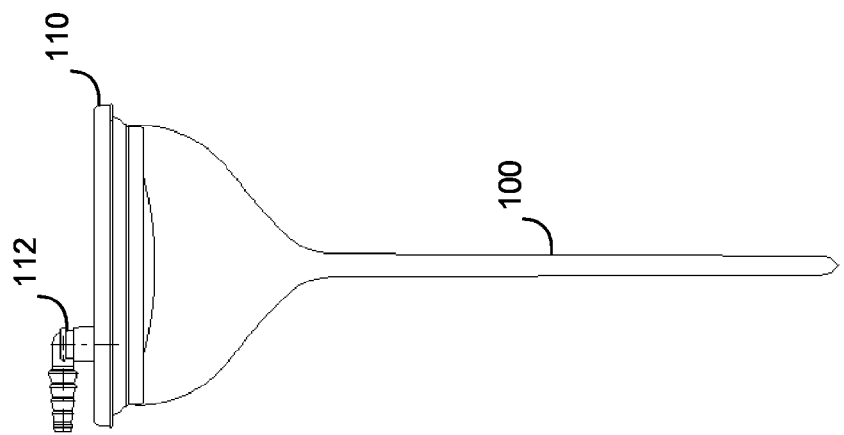
FIG. 2 is a side view of the suction bag arrangement of FIG. 1.

FIG. 2 shows the suction bag of FIG. 1 rotated 90 degrees, i.e. seen from a direction of observation parallel to the sealed bottom. It can be seen that the width of the suction bag in a direction perpendicular to the seaming of the bottom may be significantly less than in the direction of observation of FIG. 1.

Figure 3:
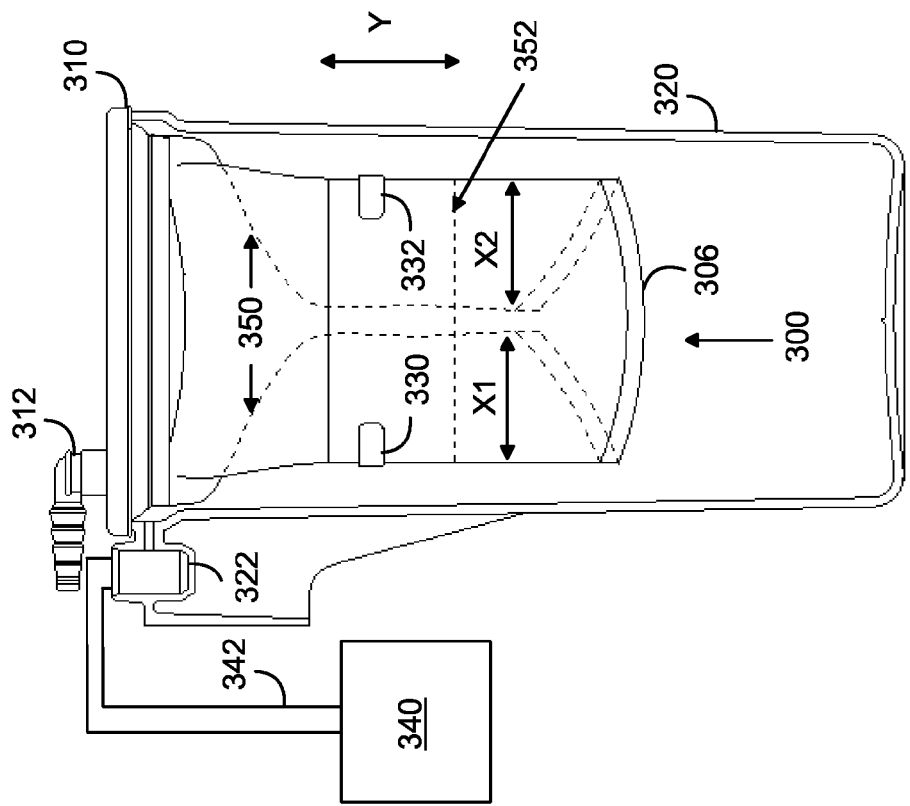
FIG. 3 shows a second embodiment of a suction bag arrangement.

FIG. 3 shows a second embodiment of a suction arrangement comprising a suction bag 300 fastened to a cover 310, and a suction canister 320. In the situation shown in FIG. 3, the suction canister 320 is closed with the cover 310, whereby the suction bag 300 fastened to the cover is settled inside the suction canister 320.

The suction bag 300 of FIG. 3 is narrowed by folding in both the lateral and longitudinal directions. The lateral direction may be determined to be the direction of the sealed bottom 306 of the suction bag, for example. Thus, the lateral direction is a direction parallel to the direction defined by the plane of the cover 310. Herein, as a specification, the plane of the cover 310 refers to the plane defined by the edges of the cover, for example, since the shape of the cover may be concave, for example, in such a manner that part of the cover settles inside the suction canister to ensure the tightness of the cover. The longitudinal direction of the suction bag 300 may be defined as a direction perpendicular to the direction of the plane defined by the cover 310.

The figure shows that the suction bag is folded in such a manner that, in the lateral direction, the suction bag 300 is at least partly narrower than the diameter of the suction canister 320, and, consequently, also that of the cover 310. The lateral folding with respect to the opened state of the suction bag is illustrated with dashed lines 350, i.e. the length of one edge of the lateral fold is X1 and X2 at the other side, the total lateral narrowing being X1+X2. The magnitudes X1 and X2 may be equal or different or the bag may be folded on one side only.

The width of the upper portion of the suction bag, from which the suction bag is fastened to the cover, is substantially equal to the width of the diameter of the lower portion of the cover if the fastening welding of the bag is implemented by welding the bag around the lower portion of the cover. However, the lateral measure of the bag, in the portion below the welding, is substantially narrowed in the manner indicated by FIG. 3.

Since the width of the suction bag 300 is narrower than the diameter of the suction canister 320, the bag does not touch the edges of the open end of the suction canister laterally, and thus does not interfere with the placement of the cover 310 in place into the suction canister 320.

In the embodiment of FIG. 3, the suction bag is folded also in the longitudinal direction of the bag, which is illustrated by a dashed line 352. The length of the fold is shown by Y, i.e. the suction bag is threefold along the stretch Y. The fold may be implemented with one fold, for example, whereby the folded length of the bag is for instance 20 to 50% shorter than the opened length. This results in the bottom of the suction bag 300 not touching the bottom of the suction canister 320 when the suction canister 320 is closed with the lid 310. Accordingly, when the suction bag is folded in both the lateral and longitudinal directions, the suction bag is easy to place into the vessel and the placement may be accomplished without placement errors.

The keeping of the fold is ensured by fastening means 330, 332. The invention is not limited to what said fastening means are. As examples of fastening means, tape, glue, other gripping means, and a mechanical connector may be mentioned.

In an embodiment, both the lateral and the longitudinal folds are kept in place with the same fastening means. This allows the number of necessary fastening means to be minimized. In another embodiment, the lateral and longitudinal folds are kept in place with separate fastening means.

The invention is neither limited to how many fastening means are used in the maintenance of the folding. In an embodiment, the folding of the suction bag is kept in place with two fastening means placed at the same height in the longitudinal direction. The fastening point may be substantially the longitudinal middle point of the bag, for example.

The suction bag may be manufactured from polyethylene or polypropylene, for example. The suction canister may be manufactured from polycarbonate and thermoplastic elastomer, for example. The volumes of the suction bags and the suction canisters may be between 1,000 and 3,000 millilitres, for example.

FIG. 3 also shows an underpressure apparatus 340. The underpressure apparatus 340 implementing the underpressure is connected to an underpressure connector 322 in the suction canister through an underpressure tube 342. The underpressure may be implemented inside the bag, and in the space between the suction canister 320 and the suction bag 300. The underpressure apparatus and other solutions required for implementing the underpressure may be made by prior art means.

Figure 4:
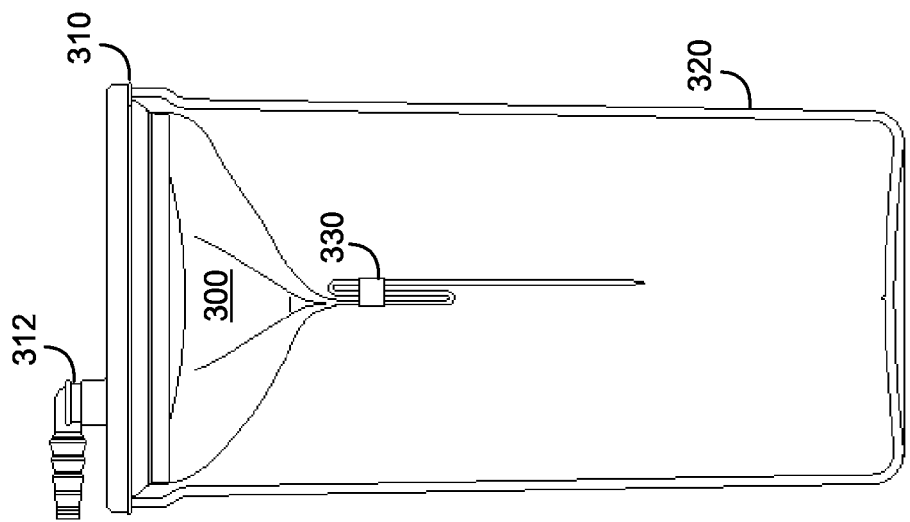
FIG. 4 illustrates the suction arrangement of FIG. 3, observed from the side.

FIG. 4 illustrates the suction bag arrangement of FIG. 3, seen from the side. The figure shows that the suction bag 300 is folded once in the longitudinal direction and is kept in place by means of a fastening means 330. The figure shows that when the suction bag is settled into the suction canister, a considerable clearance still remains between the bottom of the suction bag and the bottom of the suction canister, i.e. the bottom of the suction bag does not touch the bottom of the vessel when the cover is arranged in place.

Figure 6:
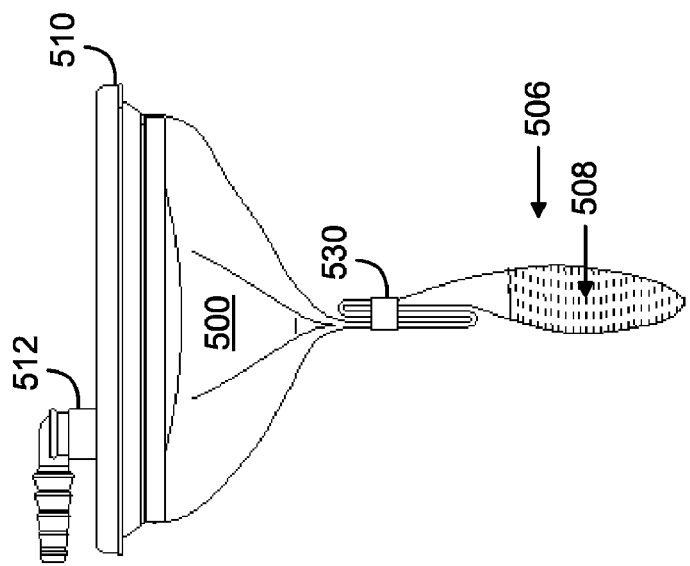
FIG. 6 illustrates the suction arrangement of FIG. 5, observed from the side.
Figure 5:
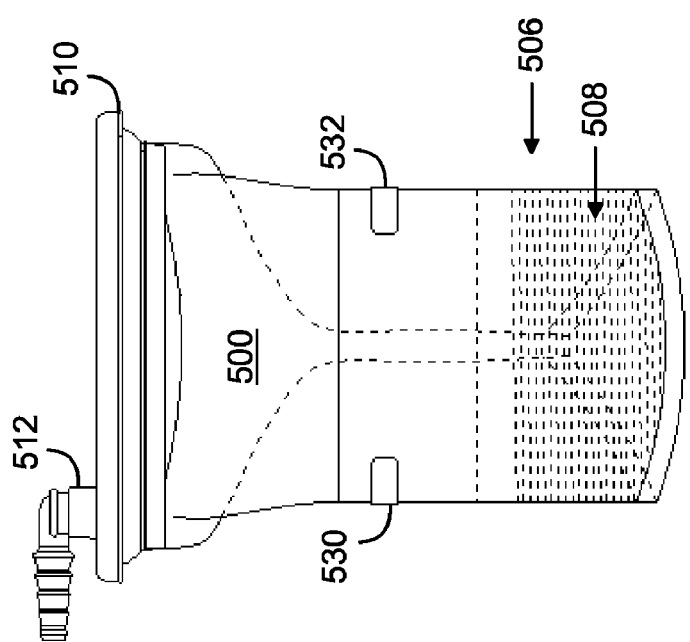
FIG. 5 shows a third embodiment of a suction bag arrangement.

FIGS. 5 and 6 show yet another embodiment of a suction bag arrangement. In connection with the use of suction bags, a functional sub-stance acting on the patient fluids may be mixed thereto, such as a solidifier agent and/or a disinfecting agent, for example. The purpose of the solidifier agent is to solidify the liquid in the suction bag, so that it does not spread widely during the removal, transport and disposal of the suction bag, should the suction bag be damaged for some reason. The purpose of a disinfecting agent, in turn, is to lessen the security risks associated with the handling of the liquid.

It is known to dose a solidifier agent into a suction bag in connection with the placement thereof through a tapped hole in the cover either as loose powder or by the use of a separate solidifier agent bag. Accordingly, dosing the solidifier agent into the suction bags has been a time-consuming process.

Alternatively, the solidifier agent is dosed into the bags already at the factory. However, in connection with storage and transport, part of the solidifier agent may be carried to the connectors between the bag and the cover. When acted upon by moisture, such solidifier agent in the connectors may clog the connectors thus preventing normal use of the bag.

FIG. 5 illustrates an embodiment for implementing the dosage of solidifier agent. In the embodiment of the figure, the suction bag is folded longitudinally in such a manner that a space 506 for a solidifier agent 508 is generated at the opposite end of the bag seen from the cover. In other words, the fold in the suction bag 500 allows the bag to be divided into at least two subspaces. This enables a substantial restriction of the solidifier agent 508 in the most distal partial space 506 seen from the cover coming into contact with the contactors in the cover 510. For example, in connection with transport and storage, the drawbacks caused by the coming into contact of the solidifier agent with the contactors can be avoided.

When the suction bag fastened to the cover is arranged in the suction canister together with the cover, the suction canister closes in an airtight manner. An underpressure system is coupled to the suction bag arrangement and it may implement the underpressure inside the suction bag and in the space between the suction bag and the suction canister. The manner of implementing the underpressure system is not crucial to the present invention, and it may thus be implemented in known manners. Under the action of the underpressure, the fastening means release the suction bag to settle into the suction canister substantially against the walls of the suction canister. The release by the fastening means refers for instance to the tapes employed to keep the fold being torn, the glue yielding or a mechanical connector releasing its grip. It is evident that the dimensioning of the strength of the fastening means is normal development work to a person skilled in the art. For example, if normal tape or pre-cut tape is used as the fastening means, the fastening force of the tape should be dimensioned in a manner allowing a predetermined underpressure to tear the tape open, thus releasing the bag to be opened into the suction canister. However, the tape should maintain the narrowing of the bag during normal handling, storage and transport.

In an embodiment, the fastening means are not opened by the use of underpressure; instead, the fastening force of the fastening means is dimensioned in a manner forcing them to open under the action of the liquid that flows into the suction bag.

If a functional substance is already dosed into the suction bag, said agent is at the bottom of the opened suction bag. This being so, the liquid flowing into the suction bag is mixed with the functional substance. The use of a functional substance, such as a solidifier agent, in connection with the use of suction bags in the manner described above is easy. Furthermore, the dosing of the solidifier agent already in connection with the factory manufacture of the suction bag ensures that a correct amount of solidifier agent is dosed, which has been difficult when loose powder is dosed.

FIG. 6 further illustrates the solution of FIG. 5, seen from the side. The figure shows the space 506 created in the area below the fastening means 530, wherein the solidifier agent 508 is dosed.

In connection with the description of the invention, the concept narrowing has been used of the function for reducing the dimensions (width, length) of the suction bag. In connection with the description, said term refers to all narrowing actions, such as folding, wrapping, rolling or scrunching.

In the above, mainly cylindrical forms of the suction canister have been referred to and described in the figures, whereby the lateral cross-section of the vessel is circular. However, the invention is not restricted to the suction canister having a circular cross-section; the shape of the vessel may be elliptical, for example, which may be advantageous for instance in confined spaces, such as an ambulance. In this case, the shape of the cover of the suction canister may also be elliptical, and the suction bag may take such a shape that it substantially fills the elliptical vessel when opening. In the case of an elliptical cover, the lateral direction of the bag may refer to the direction parallel to the longer diameter of the ellipse, for example.

It is obvious to a person skilled in the art that as technology advances, the basic idea of the invention can be implemented in a variety of ways. Consequently, the invention and its embodiments are not restricted to the above examples, but can vary within the scope of the claims.

The invention claimed is:

1. An arrangement in connection with a patient operation, comprising:
   a suction canister having an open end;
   a cover for closing the open end;
   a suction bag coupled to the cover and placeable in the suction canister for collecting material;
   a fastener for keeping the suction bag narrowed when coupled to the suction canister in such a manner that a width and a length of the suction bag, when narrowed, are smaller along at least part of the suction bag than when the suction bag is opened; and
   an underpressure apparatus for applying underpressure to a space between the suction canister, wherein when the suction bag is coupled to the suction canister, the fastener is arranged to release the suction bag to be opened into the suction canister under the action of the underpressure when the cover is closed.

2. An arrangement as claimed in claim 1, wherein the fastener is arranged to keep the suction bag narrowed in a lateral direction in such a manner that a bottom of the suction bag fits through the open end without touching edges of the open end.

3. An arrangement as claimed in claim 1, wherein the fastener is adapted to narrow the suction bag in a longitudinal direction such that when the cover rests in the suction canister, a bottom of the suction bag coupled to the cover is spaced from the bottom of the suction canister.

4. An arrangement as claimed in claim 1, wherein the fastener is adapted to simultaneously maintain a lateral and longitudinal narrowing of the suction bag.

5. An arrangement as claimed in claim 1, wherein the suction bag includes a sealed bottom defining a lateral direction of the suction bag.

6. An arrangement as claimed in claim 1, wherein a lateral direction is a direction of a plane defined by the cover, and a longitudinal direction is a direction perpendicular to the direction of a plane defined by the cover.

7. An arrangement as claimed in claim 1, wherein the suction bag is composed of a flexible plastic that yields in lateral and longitudinal directions of the suction bag.

* * * * *